(12) United States Patent  (10) Patent No.: US 8,646,341 B2
Schulten et al.  (45) Date of Patent: Feb. 11, 2014

(54) FILTRATION SYSTEM FOR GAS ANALYSIS

(75) Inventors: Armin Schulten, Timmendorfer Strand (DE); Michael Rosert, Timmendorfer Strand (DE); Benjamin Brandenburg, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 467 days.

(21) Appl. No.: 12/830,664

(22) Filed: Jul. 6, 2010

(65) Prior Publication Data

US 2011/0048107 A1  Mar. 3, 2011

(30) Foreign Application Priority Data

Sep. 3, 2009  (DE) .......................... 10 2009 039 886

(51) Int. Cl.
*G01N 1/22* (2006.01)
*B01D 53/14* (2006.01)
(52) U.S. Cl.
USPC ................ 73/863.23; 422/88; 95/90; 95/135; 95/136; 95/137; 436/100; 436/102
(58) Field of Classification Search
USPC ............. 73/31.05, 863.23; 422/69, 88; 95/90, 95/116, 135, 136, 137; 436/100, 101, 102
See application file for complete search history.

(56) References Cited

U.S. PATENT DOCUMENTS

| | | | | |
|---|---|---|---|---|
| 3,374,183 A | * | 3/1968 | Cooper ......................... | 502/346 |
| 3,433,581 A | * | 3/1969 | Hirschler, Jr. et al. ..... | 423/213.2 |
| 3,950,263 A | * | 4/1976 | Fukuma et al. ............... | 252/193 |
| 4,230,457 A | | 10/1980 | Leichnitz | |
| 4,389,372 A | | 6/1983 | Lalin | |
| 4,582,819 A | * | 4/1986 | Miller et al. .................. | 502/415 |
| 4,687,640 A | * | 8/1987 | Schillaci ....................... | 422/120 |
| 5,198,002 A | * | 3/1993 | Mei et al. ...................... | 95/275 |

(Continued)

FOREIGN PATENT DOCUMENTS

| | | |
|---|---|---|
| DE | 733 715 B | 4/1943 |
| DE | 39 08 195 C1 | 6/1990 |

(Continued)

OTHER PUBLICATIONS

J.W.H. Smith, P. Westreich, L.M. Croll, J.H. Reynolds, and J. R. Dahn, "Understanding the role of each ingredient in a basic copper carbonate based impregnation recipe for respirator carbons," Journal of Colloid and Interface Science 337 (2009) 313-321.*

(Continued)

*Primary Examiner* — Lisa Caputo
*Assistant Examiner* — Punam Roy
(74) *Attorney, Agent, or Firm* — McGlew and Tuttle, P.C.

(57) ABSTRACT

A device for gas analysis includes a detector tube (2) and can be used in the area of explosive or combustible gases. A filter material, which consists of a granular, porous material and has an impregnation for absorbing toxic gases, is provided between the detector tube (2) and a pump (6).

19 Claims, 2 Drawing Sheets

(56) References Cited

U.S. PATENT DOCUMENTS

| | | | |
|---|---|---|---|
| 5,853,681 A * | 12/1998 | Denny et al. | 423/225 |
| 7,140,232 B2 * | 11/2006 | Wright et al. | 73/25.01 |
| 7,560,413 B2 * | 7/2009 | Lok | 502/346 |
| 7,592,178 B2 * | 9/2009 | Ding et al. | 436/3 |
| 7,708,807 B2 * | 5/2010 | Honda et al. | 95/149 |
| 2002/0092339 A1 * | 7/2002 | Lee et al. | 73/23.2 |
| 2004/0112117 A1 * | 6/2004 | Wright et al. | 73/25.01 |
| 2004/0161367 A1 | 8/2004 | Truex et al. | |
| 2004/0185554 A1 * | 9/2004 | Daitch et al. | 435/309.1 |
| 2005/0056148 A1 * | 3/2005 | Sweeney et al. | 95/90 |
| 2005/0252273 A1 * | 11/2005 | Imoto | 73/23.2 |
| 2008/0053194 A1 * | 3/2008 | Ahmad | 73/25.01 |
| 2010/0275922 A1 * | 11/2010 | Brandenburg et al. | 128/205.27 |
| 2011/0004418 A1 * | 1/2011 | Chillrud et al. | 702/31 |

FOREIGN PATENT DOCUMENTS

| | | | | |
|---|---|---|---|---|
| DE | 102009039886 B3 | | 10/2010 | |
| EP | 1439387 A1 | | 7/2004 | |
| GB | 440943 A | * | 9/1934 | |
| GB | 2229111 A | | 9/1990 | |
| JP | 11169659 A | * | 6/1999 | B01D 53/56 |

OTHER PUBLICATIONS

JP 1169659 Machine Transl, Japan.*

Ilaria Rosso, Camilla Galletti, Massimo Bizzi, Guido Saracco, and Vito Specchia, "Zinc Oxide Sorbents for the Removal of Hydrogen Sulfide from Syngas," Industrial & Engineering Chemistry Research 2003 42 (8), 1688-1697.*

* cited by examiner

FILTRATION SYSTEM FOR GAS ANALYSIS

CROSS REFERENCE TO RELATED APPLICATIONS

This application claims the benefit of priority under 35 U.S.C. §119 of German Patent Application DE 10 2009 039 886.4 filed Sep. 3, 2009, the entire contents of which are incorporated herein by reference.

FIELD OF THE INVENTION

The present invention pertains to a device for gas analysis with a detector tube.

BACKGROUND OF THE INVENTION

A device for gas sampling with a detector tube is known from DE 733 715 B. A double-acting reciprocating pump, in which two pumps with hollow piston rods are arranged opposite each other, is provided for taking gas samples. A hollow housing with an insertion pipe is located between the free ends of the piston rods for receiving the detector tube. The interior space of the housing is provided with a filter mat, with which toxic substances, which have not been fully absorbed by the detector tube, are to be absorbed. Harmful gas shall be prevented with the filter mat from entering the pumps. Details of the properties of the filter mass cannot be found in DE 733 715 B.

SUMMARY OF THE INVENTION

The basic object of the present invention is to improve a device of the said type such that it can be used in the area of explosive or combustible gases.

According to the invention, a device is provided for gas analysis. The device comprises a detector tube connected to a pump for sampling gas. A filter material is provided through which flow can take place, between the detector tube and the pump. The filter material comprises a granular porous material with an impregnation for absorbing harmful gases.

Provisions are made according to the present invention for using as the filter material in the gas analyzer the porous carrier material provided with an impregnation. The porous material is mounted in a dense packing in a filter housing. Silica gel, aluminum oxide or aluminum silicate are suitable for use as porous materials.

The carrier materials mentioned according to the present invention have the advantage, for example, over activated carbon that they cannot ignite at high toxic gas concentrations. Another advantage is that organic gases and vapors can be desorbed more rapidly in a rinsing cycle.

The filter material is advantageously arranged between two plastic screens arranged opposite and two glass fabric mats. A particle filter arranged of the filter material is used to retain aerosols and dusts.

The impregnation of the porous carrier is advantageously designed to adsorb acid gases, for example, $H_2S$ or $SO_2$. The impregnating components are basic copper carbonate or basic zinc carbonate or a mixture of basic copper carbonate and basic zinc carbonate. The weight percentage of the impregnation relative to the porous carrier is up to 10%.

A process of preparing a filter material for a device for gas analysis with a detector tube is characterized by the steps of dissolving 1,000 g of basic copper carbonate with 200 g of ammonium carbonate in 4,000 mL of ammonia solution and of subsequently impregnating 16 kg of silica gel with it. The silica gel thus impregnated is subsequently dried in a drying cabinet.

An exemplary embodiment is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
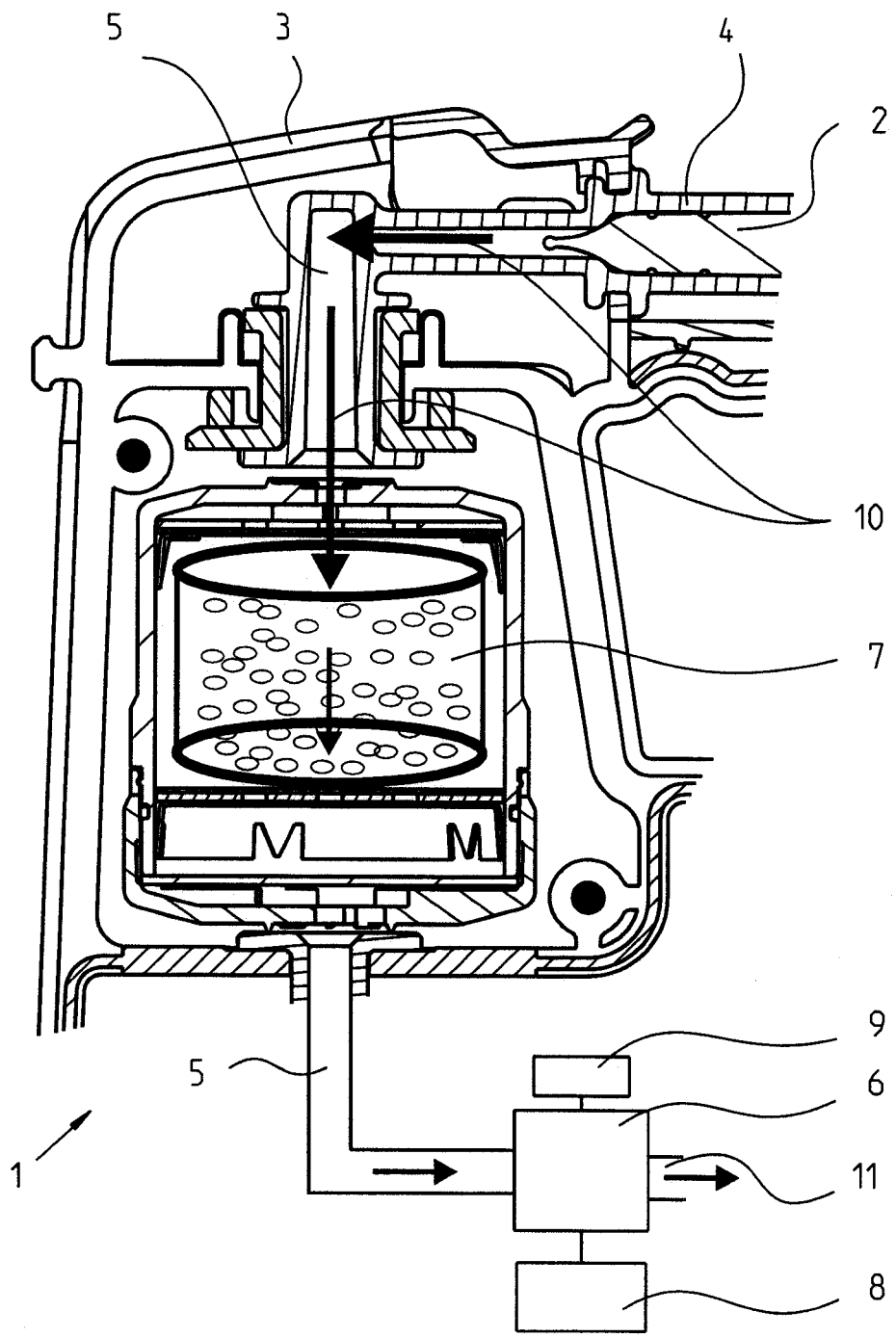
FIG. 1 is a schematic sectional view of a measuring device for gas analysis according to the invention.

Referring to the drawings in particular, FIG. 1 schematically shows a measuring device 1 for gas analysis with a detector tube 2. The measuring device 1 comprises a housing 3 with a bracket 4 for receiving the detector tube 2, with a gas duct 5 between bracket 4 and a diaphragm pump 6 and with a filter cartridge 7 in the gas duct 5 between bracket 4 and diaphragm pump 6. The diaphragm pump 6 is connected to a pump control unit 8 and a power source 9. The measured gas, drawn through the detector tube along arrows 10, leaves the diaphragm pump 6 at the measured gas outlet 11.

Figure 2:
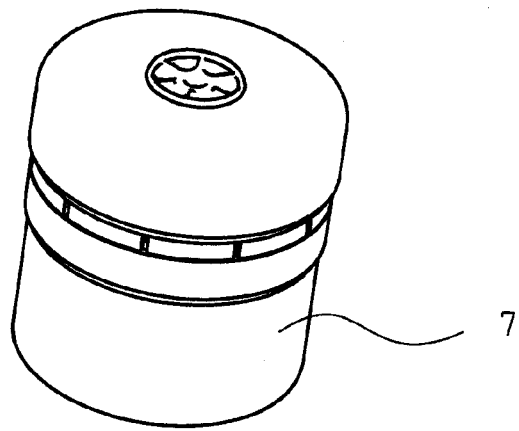
FIG. 2 is a perspective view of a filter cartridge according to the invention.

FIG. 2 shows a perspective view of the filter cartridge 7.

Figure 3:
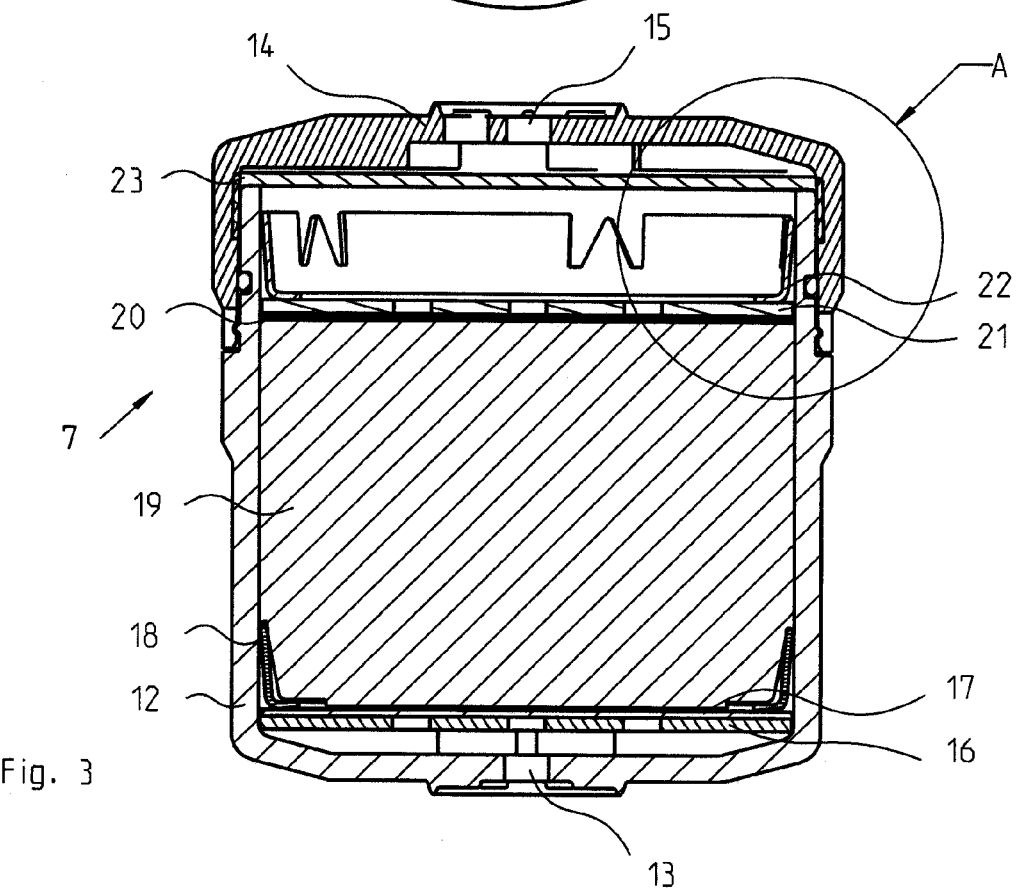
FIG. 3 is a longitudinal sectional view of the filter cartridge according to FIG. 2.

FIG. 3 shows the filter cartridge 7 according to FIG. 2 in a longitudinal section. Filter cartridge 7 comprises a pot-shaped filter housing 12 with a gas inlet 13 and a filter cover 14 with a gas outlet 15. Filter cover 14 is connected to the filter housing 12 in a gas- and liquid-tight manner. A first plastic screen 16 with a first glass fabric mat 17 placed on it, which are braced by means of a first snap ring 18, is located at the bottom of filter housing 12. This is topped by the filter material 19 consisting of a granular bulk material formed by impregnated silica gel. The filter material 19 is covered with a second glass fabric mat 20 and a second plastic screen 21, which are braced by means of a second snap ring 22 in relation to the filter housing 12, so that the filter material 19 is mounted in a dense packing in the filter housing 12. A particle filter 23, which is fixed to the filter housing 12 with the filter cover 14, is located on the top side of filter housing 12.

Other porous carrier materials may be provided for the filter material 19. In each case in the porous carrier is provided with an impregnation. According to other preferred embodiments, instead of the silica gel, aluminum oxide or aluminum silicate are used as porous materials.

The carrier materials mentioned according to the present invention have the advantage, for example, over activated carbon that they cannot ignite at high toxic gas concentrations. Another advantage is that organic gases and vapors can be desorbed more rapidly in a rinsing cycle.

Figure 4:
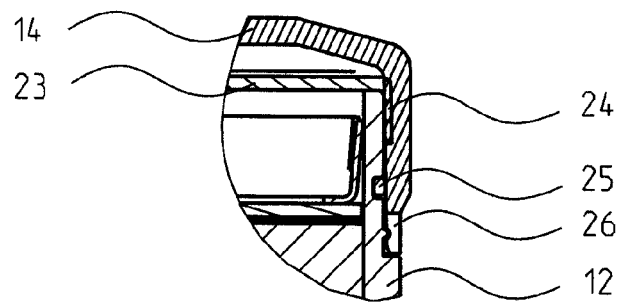
FIG. 4 is a detail view of the region labeled A of the filter cartridge according to FIG. 3.

FIG. 4 shows detail A according to FIG. 3. Identical components are designated by the same reference numbers as in FIG. 3. A particle seal 24 is located between the filter cover 14 and the filter housing 12 in the area of particle filter 23, followed by an O-ring seal 25 as a gas seal and a closure 26, which fills the free space between the filter cover 14 and the filter housing 12 and brings about a liquid-tight closure.

The filter material 19 is impregnated such that 1,000 g of basic copper carbonate with 200 g of ammonium carbonate are dissolved in 4,000 mL of ammonia solution while gently heating. Then, 16 kg of granular silica gel are impregnated with the solution and subsequently dried in a drying cabinet.

While specific embodiments of the invention have been described in detail to illustrate the application of the principles of the invention, it will be understood that the invention may be embodied otherwise without departing from such principles.

APPENDIX

List of Reference Numbers

1 Measuring device
2 Detector tube
3 Housing
4 Bracket
5 Gas duct
6 Diaphragm pump
7 Filter cartridge
8 Pump control unit
9 Power source
10 Arrow
11 Measuring outlet
12 Filter housing
13 Gas inlet
14 Filter cover
15 Gas outlet
16 First plastic screen
17 First glass fabric mat
18 First snap ring
19 Filter material
20 Second glass fabric mat
21 Second plastic screen
22 Second snap ring
23 Particle filter
24 Particle seal
25 O-ring seal
26 Closure

What is claimed is:

1. A gas analysis device for analyzing a gas sample, the device comprising:
    a housing with a detector tube receiving bracket;
    a detector tube mounted in the detector tube receiving bracket, said detector tube absorbing gases in the gas sample;
    a gas duct connected to the bracket;
    a filter cartridge connected to the gas duct, said filter cartridge being separate from said detector tube;
    a pump for sampling gas, the filter cartridge being in operative connection with the detector tube and the pump;
    filter material through which gas flows between the detector tube and the pump, the filter material being provided in the filter cartridge, the filter material comprising a granular porous material with an impregnation for absorbing particular gases, said impregnation including basic copper carbonate, basic zinc carbonate or a mixture of copper carbonate and zinc carbonate as an impregnating component, said granular porous material consisting essentially of at least one of silica gel, aluminum oxide and aluminum silicate; and
    a particle filter arranged upstream or downstream of the filter material in the filter cartridge, the particle filter absorbing aerosols or dusts.

2. A device in accordance with claim 1, further comprising:
    firm packing; and
    holding screens, wherein the filter material is mounted between the holding screens in the firm packing within the filter cartridge.

3. A device in accordance with claim 1, wherein the weight percentage of basic impregnating components relative to the filter material is up to 10%.

4. A device in accordance with claim 1, wherein:
    said detector tube provides a detection of a gas in the sample.

5. A device in accordance with claim 1, wherein:
    said impregnation is formed by dissolving 1,000 g of basic copper carbonate with 200 g of ammonium carbonate in 4,000 mL of ammonia solution; and
    16 kg of silica gel as the granular porous material is impregnated with the impregnation and then dried.

6. A device in accordance with claim 1, wherein:
    said impregnation includes basic zinc carbonate as an impregnating component.

7. A device in accordance with claim 6, wherein the impregnation includes an impregnation for absorbing acid gases.

8. A device in accordance with claim 6, wherein the impregnation for absorbing acid gases absorbs at least one of $H_2S$ and $SO_2$.

9. A process for analyzing sampled gases in an area of combustible gases, the process comprising the steps of:
    providing a detector tube adapted to absorb gases in the sampled gas;
    providing a filter material comprising a granular porous material with an impregnation for absorbing particular gases, said impregnation including basic copper carbonate, basic zinc carbonate or a mixture of copper carbonate and zinc carbonate as an impregnating component, said filter material being separate from said detector tube, said granular porous material including aluminum silicate;
    providing a pump for flowing the sampled gases;
    flowing the sampled gases first through said detector tube, then through the filter material, and then through the pump, said detector tube, said filter material and said pump being arranged in the area of the combustible gases.

10. A process in accordance with claim 9, wherein:
    said providing of said filter material includes forming said impregnating material by dissolving 1,000 g of basic copper carbonate with 200 g of ammonium carbonate in 4,000 mL of ammonia solution; and
    said providing of said filter material includes providing 16 kg of silica gel as the granular porous material being impregnated with the impregnating material and then dried.

11. A process in accordance with claim 9, further comprising:
    providing a particle filter arranged upstream or downstream of said filter material, said particle filter absorbing aerosols or dusts.

12. A process in accordance with claim 9, wherein:
    said impregnation includes basic zinc carbonate as an impregnating component.

13. A process in accordance with claim 12, wherein:
the sampled gas includes acid gases.

14. A process in accordance with claim 12, wherein:
the sampled gas includes one of $H_2S$ and $SO_2$.

15. A process in accordance with claim 9, further comprising:
providing a firm packing;
providing holding screens; and
mounting the filter material between the holding screens in the firm packing.

16. A process in accordance with claim 9, wherein:
a weight percentage of basic impregnating material relative to the granular porous material is up to 10%.

17. A process in accordance with claim 9, wherein:
said detector tube provides a detection of a gas in the sample.

18. A process for analyzing sampled gases in an area of combustible gases, the process comprising the steps of:
providing a detector tube adapted to absorb gases in the sampled gas;
providing a filter material comprising a granular porous material with an impregnation for absorbing particular gases, said impregnation including basic copper carbonate, basic zinc carbonate or a mixture of copper carbonate and zinc carbonate as an impregnating component, said filter material being separate from said detector tube;
providing a pump for flowing the sampled gases;
flowing the sampled gases first through said detector tube, then through the filter material, and then through the pump, said detector tube, said filter material and said pump being arranged in the area of the combustible gases;
said providing of said filter material includes forming said impregnating material by dissolving 1,000 g of basic copper carbonate with 200 g of ammonium carbonate in 4,000 mL of ammonia solution; and
said providing of said filter material includes providing 16 kg of silica gel as the granular porous material being impregnated with the impregnating material and then dried.

19. A gas analysis device for analyzing a gas sample, the device comprising:
a housing with a detector tube receiving bracket;
a detector tube mounted in the detector tube receiving bracket, said detector tube absorbing gases in the gas sample;
a gas duct connected to the bracket;
a filter cartridge connected to the gas duct, said filter cartridge being separate from said detector tube;
a pump for sampling gas, the filter cartridge being in operative connection with the detector tube and the pump;
filter material through which gas flows between the detector tube and the pump, the filter material being provided in the filter cartridge, the filter material comprising a granular porous material with an impregnation for absorbing particular gases, said impregnation including basic copper carbonate, basic zinc carbonate or a mixture of copper carbonate and zinc carbonate as an impregnating component, said granular porous material consisting essentially of at least one of silica gel, aluminum oxide and aluminum silicate;
firm packing; and
holding screens, wherein the filter material is mounted between the holding screens in the firm packing within the filter cartridge.

\* \* \* \* \*